US007453254B2

(12) United States Patent
Weber et al.

(10) Patent No.: US 7,453,254 B2
(45) Date of Patent: Nov. 18, 2008

(54) MICROSTRUCTURED CHEMICAL SENSOR

(75) Inventors: Heribert Weber, Nuertingen (DE); Doris Schielein, Gomaringen (DE); Christian Krummel, Kirchentellinsfurt (DE); Christoph Schelling, Reutlingen (DE)

(73) Assignee: Paragon AG, Delbruck (DE)

(*) Notice: Subject to any disclaimer, the term of this patent is extended or adjusted under 35 U.S.C. 154(b) by 0 days.

(21) Appl. No.: 10/565,984

(22) PCT Filed: Jul. 23, 2004

(86) PCT No.: PCT/DE2004/001647

§ 371 (c)(1), (2), (4) Date: Feb. 12, 2007

(87) PCT Pub. No.: WO2005/012893

PCT Pub. Date: Feb. 10, 2005

(65) Prior Publication Data

US 2007/0234801 A1 Oct. 11, 2007

(30) Foreign Application Priority Data

Jul. 25, 2003 (DE) ................................ 103 33 996
Oct. 13, 2003 (DE) ................................ 103 47 415

(51) Int. Cl.
*G01N 27/00* (2006.01)
*G01N 27/12* (2006.01)

(52) U.S. Cl. .................................. 324/71.1; 73/335.02

(58) Field of Classification Search ................ 324/71.1; 73/335.02
See application file for complete search history.

(56) References Cited

U.S. PATENT DOCUMENTS 5,563,102 A * 10/1996 Michael ............... 257/E23.167
5,693,565 A * 12/1997 Camilletti et al. .... 257/E21.508
6,361,716 B1 * 3/2002 Kleyer et al. ................ 252/514
6,551,248 B2 * 4/2003 Miller ................. 257/E27.006
6,787,047 B1 9/2004 Hahn et al. .................... 216/2
2002/0014415 A1 * 2/2002 Nakayama et al. .......... 205/317
2002/0084885 A1 * 7/2002 Wienand et al. .............. 338/25

* cited by examiner

*Primary Examiner*—Timothy J Dole
(74) *Attorney, Agent, or Firm*—Andrew Wilford

(57) ABSTRACT

A chemical sensor has a substrate, a first metallization plane on the substrate, an electrode structure formed in the first metallization plane, a passivation layer applied to the first metallization plane and formed with contact holes, a sensitive ceramic layer on the passivation layer and in the contact holes, and a bond-promoting layer configured as a second metallization plane and between the passivation layer and the ceramic layer.

10 Claims, 3 Drawing Sheets

8 (IDT2)
9
7
6
3'
3
4
IDT1
(IDT2)
5
1
2

9
8 (IDT2)
7
6
3'
3
4
IDT1
(IDT2)
5
1
2

MICROSTRUCTURED CHEMICAL SENSOR

CROSS REFERENCE TO RELATED APPLICATIONS

This application is the US national phase of PCT application PCT/DE2004/001647, filed 23 Jul. 2004, published 10 Feb. 2005 as WO 2005/012893, and claiming the priority of German patent application 10333996.5 itself filed 25 Jul. 2003 and German patent application 10347415.3 itself filed 13 Oct. 2003, whose entire disclosures are herewith incorporated by reference.

FIELD OF THE INVENTION

The invention relates to a chemical sensor with a first metallization plane arranged on a substrate and in which an electrode structure is formed, a passivation layer structured with contact holes applied to the first metallization plane and a sensitive ceramic layer which is applied to the passivation layer and in the contact holes by means of dispensing application, silk screening or ink jet processes followed by sintering.

BACKGROUND OF THE INVENTION

Chemical sensors in which the electrical resistance of a sensitive layer, usually comprised of metal oxides, can be evaluated with the aid of an evaluating structure formed by the electrodes, are known in a wide variety of configurations especially for use as gas or moisture sensors. As sensitive layers for gas detection, as a rule, porous ceramic layers, for example $SnO_2$ or $WO_3$ are used because their electrical surface conductivity varies with adsorption of gases. The porous ceramic layers can be made selectively sensitive to certain gases by the use of doping agents.

The resistivity of such ceramics is very high. As a result the measurement resistance is also large. The evaluation structure, comprised usually of an interdigital structure (IDT; "Interdigitated Transducers"), may have two coplanar electrodes with fingers which interdigitate in their plane. This corresponds to parallel networks with different polarities between the two fingers across resistances which thereby have a reduced internal sensor resistance or increased sensitivity of the sensor.

Generally apart from the electrodes and the heating resistance, a temperature measurement resistance can be provided for the sensor, whereby all of the metallization elements can be structured in a single metallization plane and, for example, can be composed of platinum. To reduce the aging effect, especially of the temperature measurement resistance, in many cases a passivation layer is applied to the metallization plane, typically of silicon oxide. The passivation layer can be structured by contact holes through which contact is enabled between the electrodes and the sensitive layer applied to the passivation layer.

While the metallization and sensitive layer structures are conventionally applied to an aluminum oxide substrate, micromechanical membrane sensors are also known which use as a basis, a silicon substrate. By thermal decoupling of the sensor structure on the membrane from the substrate, the sensor can have a reduced power consumption.

A microstructured silicon membrane sensor with a sensitive layer applied to an $SiO_2$, $Si_3N_4$ membrane is known for example from DE 197 10 358 (U.S. equivalent U.S. Pat. No. 6,787,047). With this known sensor, in contrast to the sensor of the invention, only the heater and temperature measurement structures are passivated with a silicon oxide layer which is applied to an interdigitated three dimensional electrode structure and in which the sensor layer is applied by a silk screen technique to fill in the electrode structure.

In general with silk-screen formation of the sensitive ceramic layer, the layer is in the form of a thick film paste which must then be sintered. The result can be mechanical stresses which may arise or remain, especially in the form of interfacial or boundary layer stresses which can result in separation of the layer material and the generation of particles. The effect of for example $SnO_2$ or $WO_3$ on micromechanical processes is unclear so that in general a contamination danger arises.

While the porosity of the metal-oxide ceramic which results from the sintering is desirable, on the one hand since the high sensitivity depends upon the high surface volume ratio, on the other hand the porosity has a negative effect on the mechanical stability of the layer. The most important requirement for stability is that the ceramic layer and the electrodes remain adherent to their support surfaces over the life of the sensor. Furthermore, the electrical contact between the ceramic and the electrodes should not degenerate.

Up to now, the ceramic layers have been applied directly to the passivation layer. It has been found however that the adhesion of the ceramic in many instances is insufficient.

OBJECT OF THE INVENTION

It is the object of the invention to improve the situation with respect to the adhesion.

SUMMARY OF THE INVENTION

This object is achieved in accordance with the invention with a chemical sensor having a bond-promoting layer configured as a second metallization plane and located between the passivation layer and the ceramic layer.

The invention forms the improved chemical sensor in that an adhesion-promoting layer is provided, configured as a second metallization plane located between the passivation layer and the ceramic layer.

Because of the metallization applied in two layers as mentioned above it is possible to bond the porous sensitive ceramic layer better to the support for it provided by the passivation layer. Simultaneously in the upper plane between each tow contact hole openings in the metallic adhesion-promoting layer there is a locally sharply limited development of electric field lines and thus also reduced current paths between two interdigitating electrode fingers so that there is also a sharp limitation of the active zone in the sensitive ceramic which provides the advantage of improved protection against sensor poisoning, for example, by silicon. The invention, therefore, opens up the possibility of active electrical utilization of the second metallization plane, especially but not only in association with the sensor electrodes. The adhesion-promoting layer can because of its suitability as a bond material also be utilized in the bonding region of the sensor.

Advantageously the second metallization plane is so applied that it can come to lie upon the first metallization plane in the contact holes.

It can be useful to provide a further passivation layer between the bond-promoting layer and the ceramic layer and to so structure the further passivation layer that the bond-promoting layer is partially passivated.

It can also be provided that in the electrode structure of the first metallization plane two to coplanar electrodes are structured and that the second metallization plane does not lie at a defined electrical potential. In this case the advantages include those of improved adhesion and a localization of the functional ceramic zone by equipotential surfaces.

Alternatively however it can also be provided that the electrode structure of the first metallization plane forms a first electrode and the second metallization plane is configured as a second electrode and lies at a defined electrical potential so that the sensitive ceramic layer is provided with a vertical electrode arrangement. This can result in a significantly shorter electrode spacing by comparison with conventional lithographically generated lateral spacings. On the other hand the lateral extent of the ceramic layer is no longer determined by the electrode layout requirements and can be possibly reduced. In this connection it can be especially useful to configure the electrodes as iterdigitating electrodes although all other configurations of the electrodes are also possible.

Advantageously in the first metallization plane, in addition to the electrode structure, a heating structure and a temperature measuring structure can be provided.

Preferably the structures of the metallization are provided on the front side of an Si substrate which has a membrane.

BRIEF DESCRIPTION OF THE DRAWING

The invention is described in greater detail in the following based upon a number of embodiments with reference to the figures of the accompanying drawing. They show.

SPECIFIC DESCRIPTION

Figure 1:
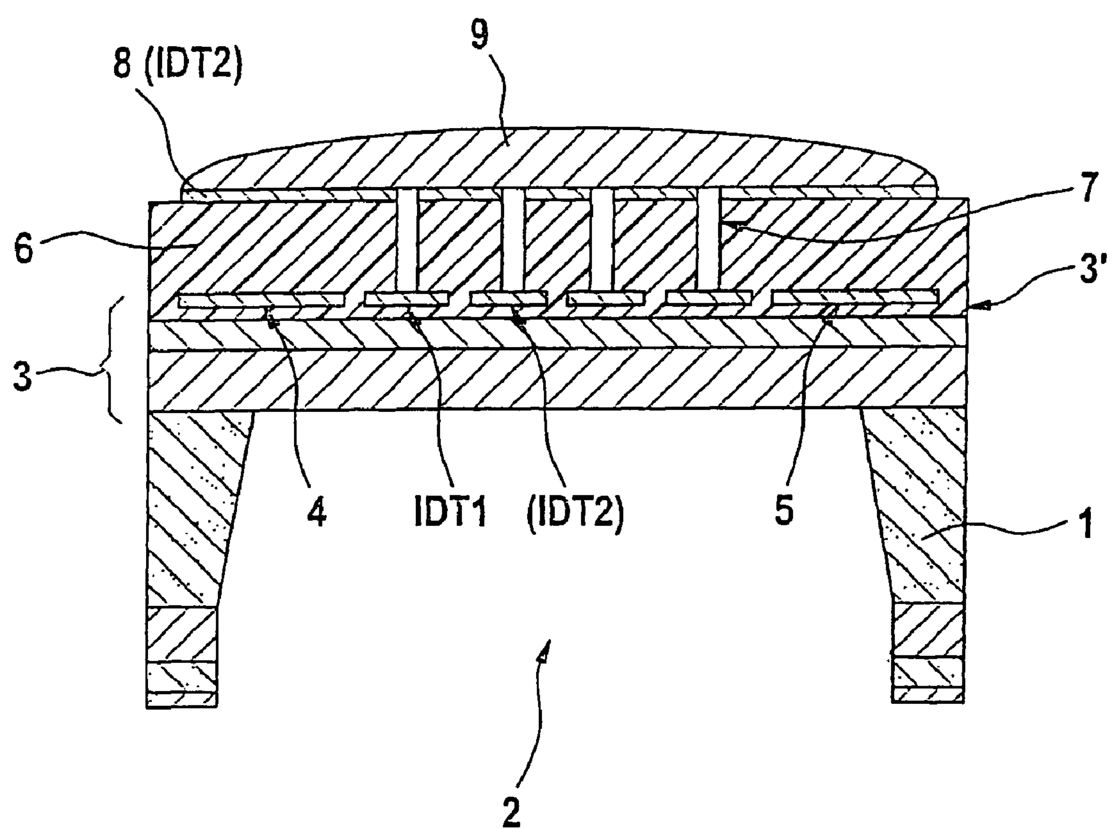
FIG. 1 a cross section of the sensor according to the invention.

FIG. 1 shows a silicon substrate 1 in which, by etching, a cavity 2 is formed in the back side of the substrate 1 to form a dielectric membrane 3 which can be comprised of a layer sequence 1 of for example silicon dioxide and silicon nitride. Above the membrane 3 there is a first metallization plane, for example of the material platinum. This metallization is so structured that the heating structure 4 and the interdigitating electrode fingers of different polarity IDT1 and IDT2 as well as, optionally, a temperature resistance 5 for the chemical sensor are formed or configured therein. For improved adhesion of the platinum metallization of the first metallization plane, it is advantageous to convert the uppermost membrane layer, here silicon nitride, at its surface into a silicon oxide layer 3'.

Above the first metallization plane lies a passivation layer 5 (intermediate insulating layer) of for example chemical-vapor-deposited (CVD) oxide, nitride or oxynitride. In the passivation layer 6 there are holes 7 which serve to contact the ceramic layer and the bond lands. On the passivation layer 6 lies a second metallization plane, the bond-promoting layer 8, which serves to enhance the bond to and for the ceramic layer 9 and which, as described further below in connection with FIG. 3, optionally lies at a defined potential and can serve as a second interdigital electrode IDT2, whereby, in this case, the first metallization plane with respect to the evaluation structure, only shows interdigital electrode fingers IDT1 of the same polarity.

Figure 2:
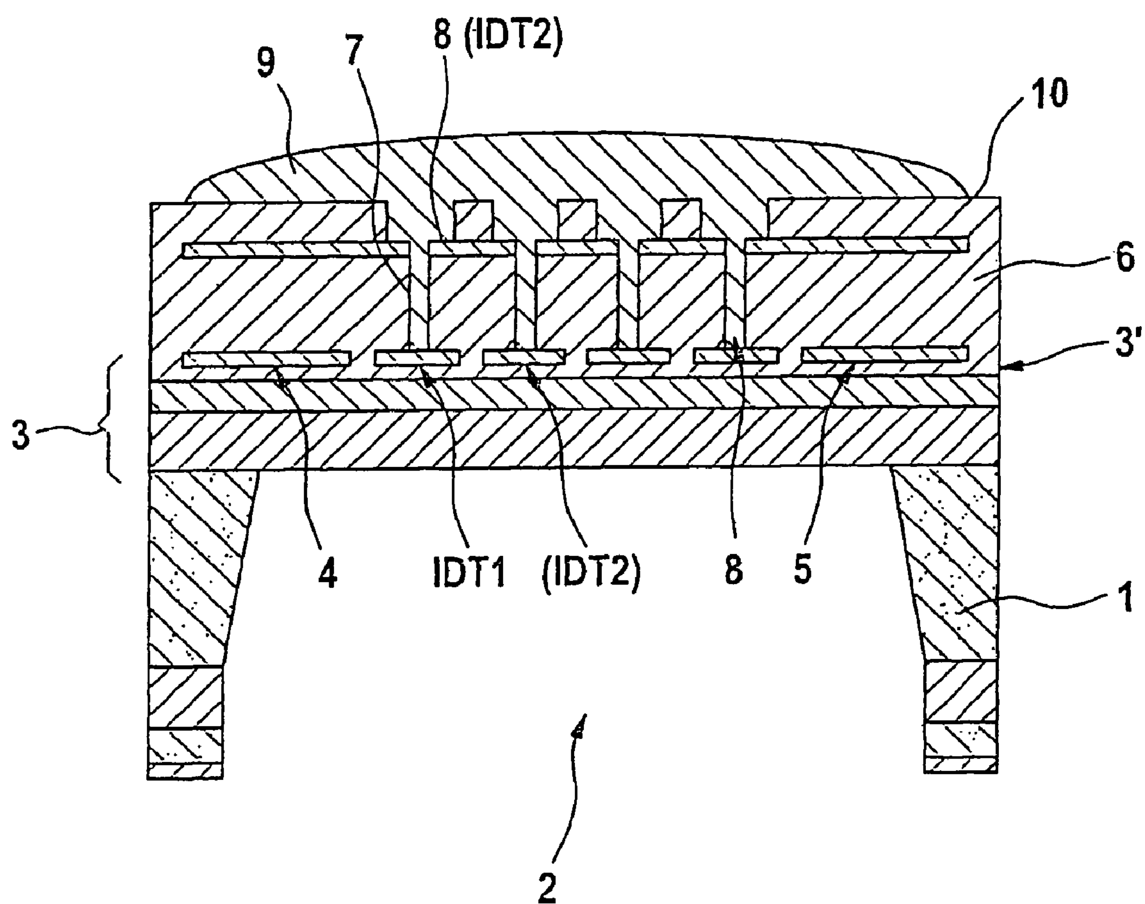
FIG. 2 in the same illustration, a variant of the sensor.

As FIG. 2 shows, the second metallization plane can be so applied that it comes to lie on the first metallization plane in the contact hole openings 7. A further passivation layer 10 can optionally lie on the second metallization 8. It contains additional holes for connection purposes.

To produce the sensor according to the invention, the raw silicon wafer is initially thermally oxidized. Then, using low pressure chemical-vapor deposition (LPCVD) LPCVD-nitride is deposited or an oxide is generated. Thereafter, on the front side of the wafer, deposition of the first metallization is carried out and is structured into heater 4, temperature sensor 5 and interdigital electrode IDT. Then a passivation layer 6 is applied, for example a CVD oxide (chemical-vapor deposition oxide). On the back side of the wafer an etching mask is defined for the cavity etching to produce the membrane 3. Because of the reduced thermal conductivity, the sensor is more rapidly controllable. Next the bond-promoting layer 8 or the second metallization plane is applied, for example of one or more of the materials Au, Cr/Au, Pt, Pd, W or Sn. The bond-promoting layer 8 is then so structured that it only remains in the region between the interdigitating electrode fingers on which the ceramic is intended to adhere and optionally should coincide with the bond lands.

On the front side of the wafer the contact holes 7 are then etched in the passivation layer 6 and for that purpose, the bond-promoting layer 8 can function in part as an etching mask. The application of the bond-promoting layer 8 and the etching of the contact holes can also be effected in the reverse order. Finally on the front side a protective lacquer or paint can be applied and the cavity 2 produced from the rear by anisotropic etching. In conclusion the paste dot is applied and sintered in an oven to the porous ceramic layer 9. Further details and the method steps which are known in this regard can be deduced from the above mentioned publication DE 197 10 358.

Figure 3:
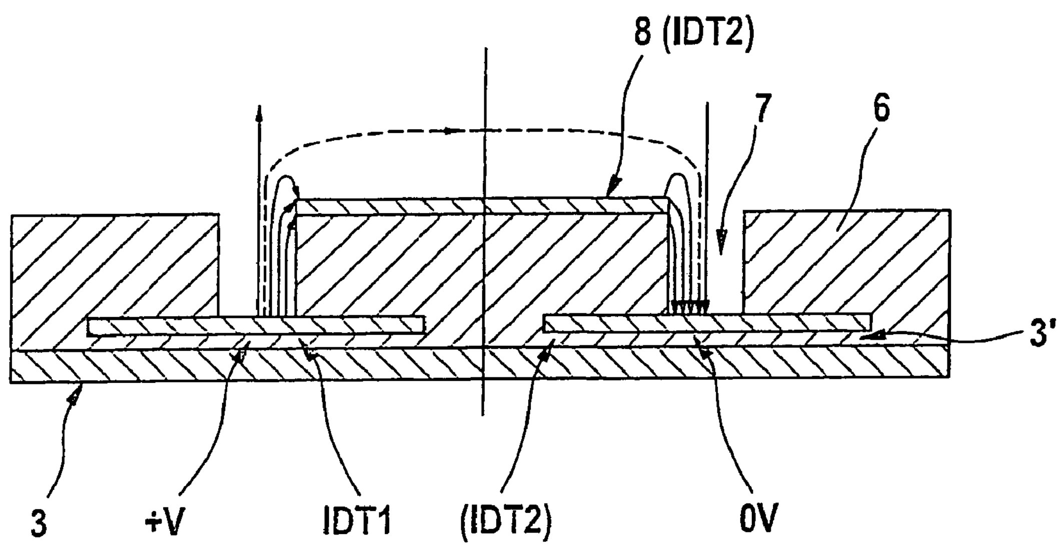
FIG. 3 in the same illustration a schematic simplified detail for the cross section of FIG. 1 or FIG. 2.

FIG. 3 shows in detail the cross section of the sensor in a portion thereof with the improved bond-promoting function according to the invention. The Z dimension is drawn to a sharply larger scale for illustration purposes and the ceramic functional layer 9 has not been illustrated for improved viewing of the parts which have been shown.

Between the two interdigital electrodes IDT1 and IDT2, a voltage is applied. The measurement signal is obtained as the current. If the upper second metallization plane which is also the structured bond-promoting layer 8 does not lie at a defined potential, that is floating, both IDT's are formed in the layer or the first metallization plane. Without the additional or second metallization or bond-promoting layer 8 the current path between with the IDTs would extend exclusively through the ceramic layer as represented in FIG. 3 by the broken line arrow. With the bond-promoting layer 8 according to the invention however it lies as shown between the bond-promoting layer 8 and the two IDT's.

The current path then runs outside the contact holes 7 through the bond-promoting layer 8. A change in conductivity in the periphery of the ceramic dot or the ceramic layer 9, for example as a result of contamination, no longer plays any practical role in this configuration, advantageously, since the electric field lines and thus the current path are locally limited by the bond-promoting layer 8.

In case the upper second metallization plane (bond-promoting layer 8) lies at a defined potential (for example 0 volts) it can be used as IDT2. The electrode spacing in this case can be effectively half as great as with a floating bond-promoting layer 8.

The invention claimed is:

1. A chemical sensor comprising:

a substrate;

a first metallization plane on the substrate;

an electrode structure formed in the first metallization plane, a passivation layer applied to the first metallization plane and formed with contact holes, a chemical-sensitive ceramic layer on the passivation layer and in the contact holes and capable of changing electrical properties when contacted by predetermined chemicals; and a bond-promoting layer configured as a second metallization plane and between the passivation layer and the ceramic layer.

2. The chemical sensor according to claim 1 wherein the second metallization plane is so applied that it comes to lie in the contact holes upon the first metallization plane.

3. The chemical sensor according to claim 1, further comprising another passivation layer between the bond-promoting layer 8 and the ceramic layer and so structured that the bond-promoting layer is partially passivated.

4. The chemical sensor according to claim 1 wherein two coplanar electrodes are formed in the electrode structure of the first metallization plane by structuring and the second metallization plane does not lie at a defined electrical potential.

5. The chemical sensor according to claim 1 wherein the electrode structure of the first metallization plane forms a first electrode and the second metallization plane is configured as a second electrode and lies at a defined electrical potential so that the sensitive ceramic layer is provided with a vertical electrode.

6. The chemical sensor according to claim 5 wherein the first and second electrodes are configured as interdigitating electrodes.

7. The chemical sensor according to claim 1 wherein a heating structure and a temperature-measuring structure are formed in the first metallization plane in addition to the electrode structure.

8. The chemical sensor according to claim 7 wherein the structures of the first metallization plane are formed on the front side of an Si-substrate which has a membrane.

9. The chemical sensor according to claim 1 wherein the material for the second metallization plane is Au, Cr/Au, Pt, Pd, W or Sn.

10. The chemical sensor according to claim 1 wherein the application of the sensitive ceramic layer is effected by silk screening, dispenser application or an ink jet process.

* * * * *